United States Patent
Ho

[11] Patent Number: 5,951,285
[45] Date of Patent: Sep. 14, 1999

[54] DENTAL SANDBLASTING CONFINER

[76] Inventor: Phillip P. Ho, 2780 State St., Suite 7, Santa Barbara, Calif. 93105

[21] Appl. No.: 08/676,650

[22] Filed: Jul. 8, 1996

[51] Int. Cl.[6] .................................................... A61C 1/16
[52] U.S. Cl. ................................. 433/116; 433/88; 604/35
[58] Field of Search ................................. 433/83, 84, 85, 433/88, 91, 116, 125; 604/35, 268; 128/846, 847; 600/119, 121

[56] References Cited

U.S. PATENT DOCUMENTS

| | | | |
|---|---|---|---|
| 1,682,784 | 9/1928 | Gythfeldt | 433/116 |
| 1,834,726 | 12/1931 | Ozon | 433/116 |
| 3,747,216 | 7/1973 | Bassi et al. | 433/91 |
| 4,286,950 | 9/1981 | Hawk | 433/116 |
| 4,424,036 | 1/1984 | Lokken | 433/116 |
| 4,692,140 | 9/1987 | Olson | 604/35 |
| 4,850,352 | 7/1989 | Johnson | 604/35 |
| 4,917,603 | 4/1990 | Haack | 433/91 |
| 5,037,431 | 8/1991 | Summers et al. | 606/131 |
| 5,122,153 | 6/1992 | Harrel | 433/91 |
| 5,154,709 | 10/1992 | Johnson | 604/35 |
| 5,197,876 | 3/1993 | Coston | 433/116 |
| 5,199,229 | 4/1993 | Harold et al. | 433/116 |
| 5,356,292 | 10/1994 | Ho | 433/116 |
| 5,376,003 | 12/1994 | Rizkalla | 433/116 |
| 5,547,376 | 8/1996 | Harrel | 433/116 |

Primary Examiner—Ralph A. Lewis
Attorney, Agent, or Firm—Jack C. Munro

[57] ABSTRACT

An improved dental sandblasting confiner in the form of a flexible walled transparent cup which has an internal chamber. The cup includes an inlet opening formed within an interior sleeve which extends within the internal chamber. A dispensing nozzle is to be conducted through the interior sleeve with the exterior surface of the dispensing nozzle forming a snug fit with the inlet opening. The tip of the dispensing nozzle is located within the internal chamber. Included within the cup and opposite the inlet opening is an access opening which is to surround a portion of the tooth that is to be repaired. Also included within the cup is an outlet opening with dispensed sand from the sandblasting tool to be discharged through the outlet opening.

3 Claims, 1 Drawing Sheet

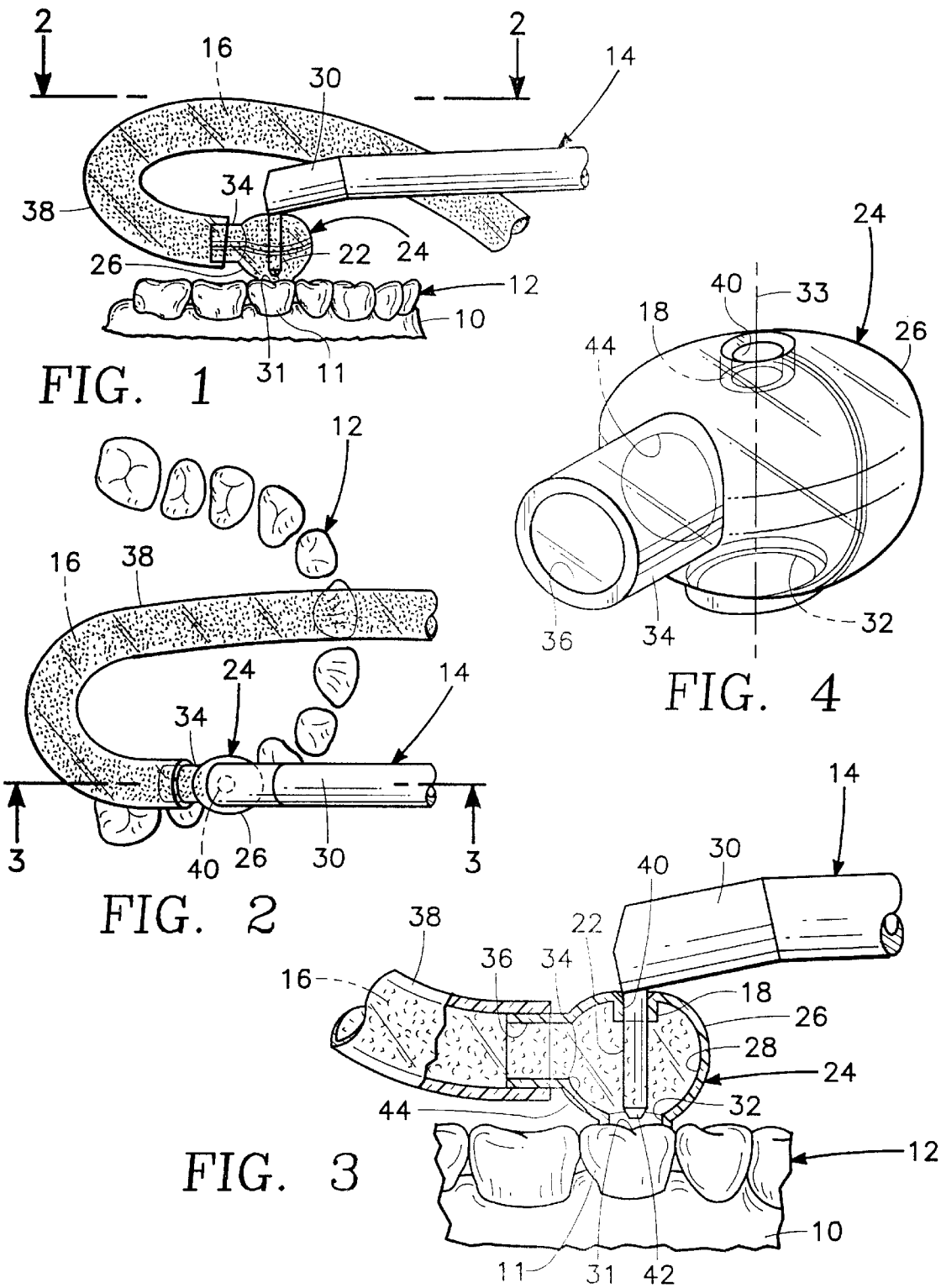

DENTAL SANDBLASTING CONFINER

BACKGROUND OF THE INVENTION

1) Field of the Invention

The field of this invention relates to dental tools and more particularly to a confiner in the form of a cup for combining and discharging dispensed sand from a sandblasting tool used to perform a drilling operation on a tooth.

2) Description of the Prior Art

Sandblasting has long been known to be an effective technique performing work against an object. Sandblasting has long been used in the construction field on cement block and stucco to remove graffiti and other stains. The same technique in recent years has been applied to a dental tool with the dental tool having a very small outlet opening which discharges a thin stream of fine sand at a high velocity. When this stream of fine sand is directed to a particular section of a tooth, such as a cavity, the abrasive nature of the sand will in essence drill away at the tooth and roughen the tooth surface. This type of sandblasting technique is especially advantageous in porcelain and composite repair as well as increasing the bond of dental composites to metal. This sandblasting technique is currently in use as a drill.

One disadvantage with sandblasting the tooth within the mouth of a human is that the dispensed sand is merely discharged within the entire mouth of the human, as well as all over the room, on the patient and dentist's clothes, eyes, etc., and other dental equipment. It is difficult to remove all of this sand even by multiple rinsings of the mouth of the human after the sandblasting procedure is ended. It would be preferable to remove the sand after it has been dispensed without it being freely thrown into all areas of the mouth of the human.

The present inventor has obtained U.S. Pat. No. 5,356,292, issued Oct. 18, 1994 to a device known as a DENTAL SANDBLASTING CONFINER. This device was a substantial improvement to not using any device at all to confine the sand as it is discharged and to remove the sand from the mouth of the human. However, the device of this patent did permit some sand to be discharged within the mouth of the human as it could not all be captured and removed. The structure of the present invention is directed to a device that will be most effective in removing almost all of the sand that is dispensed within the mouth of the human. The improved effectiveness of the present invention is achieved in part by the dentist being able to position and control the movement of both the dental sandblasting tool and the sandblasting confiner with one hand.

SUMMARY OF THE INVENTION

The structure of the present invention is directed to an improved sandblasting confiner in the form of a transparent, flexible walled cup. This cup has an inlet opening formed within an interior sleeve that is mounted within an internal chamber of the cup. Also formed within the cup is an access opening with the access opening being located opposite the inlet opening. The cup has a longitudinal center axis which connects both the center point of the inlet opening and the center point of the access opening. In between the access opening and the inlet opening is located an outlet opening. A tubular exterior sleeve is attached to the cup about this outlet opening. The dispensing nozzle is to be movable within the internal chamber and during this movement the interior sleeve maintains a snug fit at all times with the dispensing nozzle thereby preventing an escape of sand from the inlet opening.

The primary objective of the present invention is to construct a dental tool in the form of an improved sandblasting confiner so as to allow one hand operation due to friction fit of the confiner to sandblasting tool in confining dispensed sand during a dental sandblasting technique that dispenses sand within the interior of the mouth and then discharged such exteriorly of the mouth minimizing the contaminating of the areas of the mouth with the sand.

Another objective of the present invention is to construct a dental tool which can be manufactured inexpensively and thereby sold to the dental profession at a reasonable cost.

BRIEF DESCRIPTION OF THE DRAWING

FIG. 1 is a side elevational view of the improved sandblasting confiner of the present invention showing the confiner as it would be attached to a conventional sandblasting tool;

FIG. 2 is a top plan view taken along line 2—2 of FIG. 1;

FIG. 3 is a cross-sectional view taken along line 3—3 of FIG. 2 depicting usage of the sandblasting tool in conjunction with the improved sandblasting confiner of the present invention; and FIG. 4 is an exterior isometric view of the improved sandblasting confiner of the present invention.

DETAILED DESCRIPTION OF THE PREFERRED EMBODIMENT

Referring particularly to the drawing there is shown a gum 10 of a human mouth upon which are mounted a plurality of teeth 12. Within tooth 11 is located a cavity 31. A sandblasting tool 14, which is deemed to be conventional, has a conduit 30 which extends from a supply container (not shown) of sand. The sand is to be driven by air pressure through the conduit 30 and dispensed from a dispensing nozzle 22. The dispensing nozzle 22 is substantially smaller in transverse cross-sectional area than the conduit 30. The dispensing nozzle 22 extends in a substantially right angle from the conduit 30. The sand from the dispensing nozzle 22 is to be dispensed in a fine stream under a significant amount of pressure exteriorly of the tip 42 of the dispensing nozzle 22. A typical material for the sand is aluminum oxide particulates.

The improved sandblasting confiner 24 of the present invention is in the form of a cup 26. Typical material of construction for the cup 26 would be a soft plastic material with polyethylene generally being preferred. Cup 26 has an internal chamber 28. Access into the internal chamber 28 is provided through an inlet opening 40 which is formed within an interior sleeve 18. The interior sleeve 18 is located within the internal chamber 28. The dispensing nozzle 22 is to extend through the inlet opening 40 with the sidewall of the inlet opening 40 assuming a snug fit with the exterior sidewall of the dispensing nozzle 22. The dispensing nozzle 22 is located so that the tip 42 is located directly adjacent to an access opening 32. The portion of the cup 26 directly adjacent the access opening 32 is to be placed on the tooth 11 with the cavity 31 connecting with the access opening 32. With the cup 26 remaining stationary on the tooth 11, the dispensing nozzle 22 can be moved back and forth in the area of the access opening 32. This movement is so as to apply the stream of sand to all areas of the cavity 31. During this movement, the interior sleeve 18 deflects relative to the cup 26 while still maintaining a snug fit in conjunction with the dispensing nozzle 22.

The cup 26 has a longitudinal center axis 33. This longitudinal center axis 33 passes through the center point of the inlet opening 40 and also through the center point of the access opening 32. Basically, the plane of the access opening 32 is parallel to the plane of the inlet opening 40. The access opening 32 is of a larger diameter than the inlet opening 40. The portion of the cup 26 surrounding the access opening 32 is placed as best as possible in a confining manner on the tooth 11 surrounding the cavity 31 and held in that manner by the dentist or dental technician.

Connecting with the cup 26 is an outlet opening 44. Surrounding the outlet opening 44 and integrally connected with the cup 26 is a sleeve 34. The sleeve 34 has a longitudinal through hole 36. A discharge tube or hose 38 can either fit snugly or preferably just held close to the mouth of the outlet opening.

With the hose 38 connecting with, or just touching, the sleeve 34, the access opening 32 is to be located in a surrounding manner on the tooth 11 about the cavity 31. The dentist will have placed the dispensing nozzle 22 through the inlet opening 40 with the tip 42 of the nozzle being located directly adjacent the access opening 32 which now locates the tip 42 directly adjacent the cavity 31. This locating is observable by the dentist since the cup 26 is transparent. The sandblasting tool 14 is then activated with the sand 16 being dispensed and confined with the internal chamber 28. The hose 38 is to be connected to a vacuum source (not shown) so that suction is to be applied through the hose 38 to within the internal chamber 28 removing the sand 16 therefrom, pulling the sand 16 through the outlet opening 44, through through hole 36 and then through the hose 38 to a discharge location (not shown).

In actual practice, the suction hose 38 may not physically connect with the sleeve 34 but may only be placed directly adjacent the through hole 36. The body of the cup 26 can be physically trimmed in the area of the access opening 32 so that the shape of the cup 26 can be modified for the particular usage requirement. The tip 42 is to be positioned 5 to 7 millimeters from the cavity 31 during operation. While the cup 26 will catch most of the sand, it is to be understood that it is not one hundred percent effective.

What is claimed is:

1. In combination with a dental sandblasting tool comprising a housing terminating in a forward and, a dispensing nozzle extending outward from said forward end, said dispensing nozzle having an exterior sidewall, said dispensing nozzle having a free outer end defined as a tip, sand is to be discharged from said tip of said dispensing nozzle, an improved sandblasting confiner to be used with said dental sandblasting, tool as it is operated, said improved sandblasting confiner comprising:

a flexible walled cup having a wall enclosing an internal chamber, said wall having an inlet opening and an outlet opening, an interior sleeve having a through opening, said interior sleeve being integral with said wall, said through opening connecting with said inlet opening, said interior sleeve being located within said internal chamber, said exterior sidewall of said dispensing nozzle passing through said through opening and connecting in a snug fitting manner with said inlet opening and said through opening with said tip being located within said internal chamber thus allowing one hand operation of both said dental sandblasting tool and said sandblasting confiner, said flexible walled cup having an access opening spaced from both said inlet opening and said outlet opening, said tip of said dispensing nozzle being located directly adjacent said access opening with a portion of a tooth to be repaired adapted to be surrounded by said access opening, said dispensing nozzle being movable relative to the tooth within said internal chamber while said interior sleeve maintains said snug fit with said exterior sidewall of said dispensing nozzle, said dispensing nozzle also being movable relative to said wall of said flexible walled cup within said internal chamber while said flexible walled cup is fixedly positioned on a tooth with this movement of said dispensing nozzle being permitted by deflection of said interior sleeve relative to said cup, whereby sand is discharged from said tip against a portion of the tooth the sand is confined within said internal chamber and then removed therefrom through said outlet opening.

2. The combination as defined in claim 1 wherein:

said wall of said flexible walled cup being transparent.

3. The combination as defined in claim 1 wherein:

an exterior sleeve being fixedly connected to said wall at said outlet opening, whereby a discharge hose is connected to said exterior sleeve through which sand is to be discharged.

* * * * *